United States Patent
Treilhes et al.

(10) Patent No.: US 11,898,030 B2
(45) Date of Patent: Feb. 13, 2024

(54) CROSSLINKED STYRENIC BLOCK COPOLYMER

(71) Applicant: TOP GLOVE GLOBAL SDN BHD, Selangor (MY)

(72) Inventors: Sebastien Treilhes, Pulau Pinang (MY); Pierre Hoerner, Maysel (FR); Chin Guan Low, Kuala Lumpur (MY)

(73) Assignee: TOP GLOVE GLOBAL SDN BHD, Selangor (MY)

( * ) Notice: Subject to any disclaimer, the term of this patent is extended or adjusted under 35 U.S.C. 154(b) by 923 days.

(21) Appl. No.: 16/619,115

(22) PCT Filed: May 28, 2018

(86) PCT No.: PCT/IB2018/000572
§ 371 (c)(1),
(2) Date: Dec. 4, 2019

(87) PCT Pub. No.: WO2018/224881
PCT Pub. Date: Dec. 13, 2018

(65) Prior Publication Data
US 2020/0102452 A1    Apr. 2, 2020

(30) Foreign Application Priority Data

Jun. 6, 2017  (MY) .............................. PI2017702080

(51) Int. Cl.
| | | |
|---|---|---|
| *C08J 3/24* | (2006.01) | |
| *C08L 25/06* | (2006.01) | |
| *C08L 53/02* | (2006.01) | |
| *C08K 3/011* | (2018.01) | |
| *C08K 3/06* | (2006.01) | |
| *C08K 5/00* | (2006.01) | |
| *C08K 5/5397* | (2006.01) | |

(52) U.S. Cl.
CPC .............. *C08L 53/02* (2013.01); *C08J 3/242* (2013.01); *C08L 25/06* (2013.01); *C08K 3/011* (2018.01); *C08K 3/06* (2013.01); *C08K 5/0016* (2013.01); *C08K 5/0025* (2013.01); *C08K 5/5397* (2013.01); *C08L 2203/16* (2013.01); *C08L 2312/06* (2013.01)

(58) Field of Classification Search
CPC ........ C08L 53/00; C08L 53/02; C08L 53/025; C08L 53/0025
See application file for complete search history.

(56) References Cited

U.S. PATENT DOCUMENTS

| | | | |
|---|---|---|---|
| 4,341,837 A | 7/1982 | Katsuto et al. | |
| 5,093,406 A | 3/1992 | Lossner et al. | |
| 5,302,649 A | 4/1994 | Sasaki et al. | |
| 6,121,366 A | 9/2000 | Sharma | |
| 2003/0092826 A1* | 5/2003 | Pearce | B29C 48/022 524/505 |
| 2003/0118923 A1 | 6/2003 | Uzee et al. | |
| 2005/0012081 A1 | 1/2005 | Yasuda et al. | |
| 2006/0155062 A1* | 7/2006 | De Keyzer | C08F 297/044 525/88 |
| 2007/0088116 A1* | 4/2007 | Abba | A61L 15/585 524/500 |
| 2009/0186958 A1 | 7/2009 | St. Clair | |
| 2013/0260632 A1 | 10/2013 | Thomas et al. | |

FOREIGN PATENT DOCUMENTS

| | | |
|---|---|---|
| CN | 104910573 | 9/2015 |
| CN | 106633587 | 5/2017 |
| EP | 0488021 | 6/1992 |
| EP | 1472315 | 3/2007 |

OTHER PUBLICATIONS

Wang, G. et al Journal of Applied Polymer Science vol. 112 pp. 1076-1081 (Year: 2009).*
International Search Report dated Aug. 3, 2018.
Decker et al. High-Speed Photocrosslinking of Thermoplastic Styrene-Butadiene Elastomers. Journal of Applied Polymer Science, vol. 77, 1902-1912 (2000).
Zurawski et al. Characterization of Electron Beam Crosslinked Poly(Styrene-Block-Ehtylene-Co-Butylene-Block-Styrene) Polymer Engineering and Science, vol. 23, No. 9, Jun. 1, 1983. p. 510-515.
PCT/IB2018/000572 International Preliminary Report on Patentability dated Dec. 10, 2019.

* cited by examiner

*Primary Examiner* — Irina S Zemel
*Assistant Examiner* — Jeffrey S Lenihan
(74) *Attorney, Agent, or Firm* — Alston & Bird LLP

(57) ABSTRACT

Elastomeric styrenic block copolymer (SBC) compositions comprise one or more SBCs and one or more polymers miscible with styrenic end blocks of the one or more SBCs, the block copolymer compositions being both both physically and chemically crosslinked, where the chemical crosslinking comprises covalent bonds between chains of SBC and the physical crosslinking comprises non-covalent interaction between styrenic end blocks of the one or more SBCs and the one or more polymers miscible with the styrenic end blocks. The block copolymer compositions are useful in forming immersion articles such as surgical gloves.

35 Claims, No Drawings

CROSSLINKED STYRENIC BLOCK COPOLYMER

BACKGROUND OF THE INVENTION

The present disclosure relates to styrenic block copolymers which are both physically and chemically cross-linked. The copolymers find advantageous use in the manufacture of elastic dipped articles, for example gloves and condoms.

Thin-walled elastic dipped articles are traditionally made of natural rubber (NR), polychloroprene (CR), polyisoprene (IR), polyurethane (PU), nitrile butadiene rubber (NBR), styrenic block copolymers (SBC), mixtures thereof or laminations thereof.

Natural rubber is used in such applications as it is a natural product which offers exceptional performance. However, the presence of sensitizing proteins which are responsible for immediate type hypersensitivity (type I allergies) has restricted its use. To address this drawback, synthetic materials have been developed as alternatives.

Typical Processing

Thin-walled elastic films are usually shaped for the intended application (glove, condom, etc) by dipping a form of an appropriate shape into a liquid mixture of the polymer, which may be either a dispersion in water (latex) or a solution in one or more appropriate solvents. A solid film is formed following the evaporation of water or other solvents.

Enhanced performance in terms of mechanical and chemical properties, elasticity and durability of the material is achieved by a cross-linking mechanism. Vulcanization is the traditional chemical cross-linking mechanism for most elastomeric materials such as NR or IR. Vulcanization creates sulphur covalent bonds that link one polymer chain to another. However, since vulcanization with sulphur alone requires reaction conditions that are too long and requiring very high temperatures, chemical additives such as "accelerators" are added. Accelerators may be of many types and are usually classified within the following families: thiazoles, carbamates, guanidines, thiourea and thiurams. It is common practice to use a mixture of different accelerators selected from the different families to optimize the vulcanization speed and performance.

However, whereas sulphur is integrated into the polymer network through covalent bonding, accelerators are not. A typical glove formulation made of polyisoprene can comprise up to 2% of accelerators. The accelerator molecules have poor solubility in water and cannot be removed from the glove by washing. Also, they may "bloom" at the surface of the film over time, due to their limited compatibility with the rubber. Accelerators are also strong skin sensitizers and can cause allergic contact dermatitis (delayed hypersensitivity, type IV).

Product Performance

The particular combination of materials, compounding conditions and process of transformation into a thin walled film usually defines the performance of the resulting product.

NR, CR, IR and NBR are the more common elastomers and are all transformed into thin walled films starting from water dispersions, also known as lattices. However, thin walled films produced from lattices have the disadvantage that the resulting products are sometimes prone to having pinholes. These pinholes, often on the order of micrometers in diameter, may be the result of low levels of impurities in the latex which are difficult to filter out, and to the fact that the process converts a heterogeneous system (dispersion) into a film. There is some intrinsic microporosity present in the rubber which may be attributed to failure of all latex particles making up a typical film to completely coalesce with each other and form a continuous film free of interstitial voids. Native proteins (present in NR) and chemicals (surfactants, mainly in case of synthetic polymers) used for the latex stabilization and in the manufacturing process are prone to inhibit coalescence.

Advantageously, some other synthetic polymers can be dissolved in solvents, such as hydrocarbon solvents, to form a true solution. Accordingly, solvent cast technology is attractive for the production of films with extremely high-quality requirements and almost no microporosity. Pinholes are also much less likely to be present.

Multiblock rubber based copolymers, and especially styrenic block copolymer (SBCs), are particularly suitable to be used for solvent casting as they can form solutions with acceptable viscosities that can be utilised for dipping.

Styrenic Block Copolymers

SBCs are classified as thermoplastic elastomers, which possess the mechanical properties of rubbers and the processing characteristics of thermoplastics. These properties result from their molecular structure. SBCs consist of at least three blocks, generally two hard polystyrene end blocks and one soft, elastomeric (polybutadiene, polyisoprene—hydrogenated or not) midblock. More common SBCs comprise linear triblock copolymers such as styrene-ethylene/butylene-styrene (SEBS), styrene-butadiene-styrene (SBS) and styrene-isoprene-styrene (SIS), but other architectures (for example copolymers composed of more than 3 blocks) and other structures (star or radial) are also possible.

The hard and soft blocks are immiscible, so that, on a microscopic scale, the polystyrene blocks form separate domains in the rubber matrix. Therefore, SBCs exhibit two glass transition temperatures (Tg) which are characteristic of the respective homopolymer (polystyrene end-block, 90-100° C. and rubbery mid-block at around −90° C. in the case of polybutadiene, for example).

In addition to the advantages of being processed from true solution, SBCs are capable of forming elastic films with high mechanical performance without the use of any chemical cross-linking such as sulphur and accelerators, since both ends of each rubbery block are terminated by polystyrene segments and these rigid domains act as multifunctional junction points to produce a "physically" crosslinked elastomer network, similar in many respects of that of a conventional vulcanized rubber ("chemical crosslinking").

Finally, these elastomers can advantageously be formulated with suitable plasticizers to provide a desirable combination of tensile strength, elasticity and tactility, such as is required, for example, for surgical gloves.

The ultimate force at break and tensile strength are important factors in assessing the performance of thin walled extensible films such as condoms or gloves, which should be evaluated following international standards. Also, a surgical glove should provide a high sensitivity while at the same time not compressing the wearer's hand over a prolonged period of time. To prevent compression of the hand, a Modulus at 100% elongation below 1.0 MPa, and ideally below 0.7 MPa is preferred.

Suitably formulated with plasticizer, SBCs can meet all international standards and can achieve comparable, and in many cases superior, flexibility and mechanical properties to those of other elastomers such as NRL, CR, IR. This means that the material can perform mechanically in a manner comparable or superior to other elastomers while avoiding the shortcomings of latex-based elastomers such as accelerators and pinholes.

In summary, SBCs are particularly suitable for use in thin-walled film applications such as medical gloves providing excellent properties including, synthetic rubber free of natural rubber proteins, accelerator free, softness, as well as films with extremely high quality having almost no pinholes and no hydration.

Suitable compositions of SBCs for use in surgical gloves are described in EP0488021 which discloses a combination of two or more S-EB-S block copolymers and EP1472315 which discloses a combination of one S-EB-S block copolymer and one S-EP-S-EP block copolymer.

Limitations of Styrene Block Copolymers

The products made from SBCs as described in the patents referred to above possess a major shortcoming. As the network is made only of physical crosslinks, rather than chemical crosslinks, the glassy polystyrene domains soften and lose their cohesion when contacted with certain organic solvents.

For example, surgical gloves made of SBCs are destroyed when placed in direct contact with organic solvents. Several organic solvents and "aggressive" chemicals may be used in the medical field. One example is methyl methacrylate monomer (MMA) which is present in uncured bone cement used in arthroplasty. MMA has a Hansen solubility parameter of 17.9 $MPa^{1/2}$, which is close to that of PS (18.6). Another example is diethyl ether which is used as a solvent in some preparations, such as collodion. The weak chemical resistance to these solvents is a major limitation of this family of elastomers for gloves for surgical usage.

It is possible to strengthen the physical network by adding a chemical network through permanent covalent bonds joining together the chains of the elastomeric phase to give an insoluble material. An example is described in Decker et al, Journal of Applied Polymer Science (vol. 77, 1902-1912, 2000) using commercial SBS and SIS triblock copolymers cross-linked by UV irradiation in the presence of a radical-type photoinitiator. The crosslinking process may be markedly accelerated by the addition of multifunctional organic molecules such as acrylate or thiol monomers that can copolymerize with polybutadiene or polyisoprene unsaturations.

However, this chemical cross-linking process leads to a dramatic decrease of the mechanical properties of the film, as the coexistence of two networks (one "physical" and one "chemical") decreases the mechanical resistance and increases the rigidity of the material.

Such materials could not, for example, achieve the international standards for the case of surgical gloves, such as the minimum tensile strength as described in the ASTM D3577.

It would therefore be desirable to provide alternative SBC compositions and methods for their preparation that address one or more of the above highlighted problems and deficiencies.

The reference in this specification to any prior publication (or information derived from it), or to any matter which is known, is not, and should not be taken as an acknowledgement or admission or any form of suggestion that the prior publication (or information derived from it) or known matter forms part of the common general knowledge in the field of endeavour to which this specification relates.

SUMMARY OF THE INVENTION

In one aspect, the present disclosure provides an elastomeric styrenic block copolymer (SBC) composition comprising one or more SBCs and one or more polymers miscible with styrenic end blocks of the one or more SBCs; wherein said block copolymer composition is both physically and chemically crosslinked;
wherein said chemical crosslinking comprises covalent bonds between chains of SBC and;
wherein said physical crosslinking comprises non-covalent interaction between styrenic end blocks of the one or more SBCs and the one or more polymers miscible with the styrenic end blocks.

In another aspect, the present disclosure provides a miscible polymer blend comprising one or more SBCs and one or more polymers miscible with styrenic end blocks of the one or more SBCs;
wherein said miscible polymer blend is both physically and chemically crosslinked;
wherein said chemical crosslinking comprises covalent bonds between chains of SBC and;
wherein said physical crosslinking comprises non-covalent interaction between styrenic end blocks of the one or more SBCs and the one or more polymers miscible with the styrenic end blocks.

The herein disclosed unique compositions or blends comprising physically and chemically cross-linked styrene block copolymers find use in, for example, the manufacture of thin-walled dipped articles such as condoms and medical gloves. The unique compositions or blends overcome the shortcoming of chemical resistance in presently available SBCs, while maintaining a high level of mechanical resistance and flexibility.

In another aspect, the present disclosure provides an elastomeric styrenic block copolymer composition comprising:
  (a) one or more SBCs;
  (b) one or more polymers miscible with polystyrene end blocks of the one or more SBCs; and
  (c) one or more cross-linking agents capable of inducing covalent bonding between chains of the one or more SBCs.

In another aspect, there is provided a method of preparing a SBC composition comprising the step of: combining one or more SBCs, one or more polymers miscible with polystyrene end blocks of the one or more SBCs; and one or more cross-linking agents capable of inducing covalent bonding between chains of the one or more SBCs.

The compositions or blends may further comprise one or more plasticizers and/or flexibilizers compatible with the elastomeric mid-block of the one or more SBCs.

The compositions or blends may further comprise one or more compatibilizers which enhance the miscibility between styrenic end blocks of the one or more SBCs and the one or more miscible polymers. Such compatibilizers may be, for example, surfactants and particularly polymeric surfactants such as di-block copolymers comprising a PS segment, or a low molecular weight polymer or resin having an appropriate solubility parameter.

The one or more SBCs may have a fully unsaturated or partially unsaturated elastomeric mid-block or may have a fully saturated elastomeric mid-block.

The one or more SBCs may be selected from the group consisting of SIS, SBS, SIBS, S-isobutylene-S, SEBS, SEPS, SEEPS or a SBC functionalized with reactive groups grafted in the middle rubber block such as, for example, carboxylic acid, amine, alcohol, maleic anhydride, epoxy, isocyanate and aziridine groups or mixtures thereof.

Preferably, the SBC is composed of one or a mixture of SBCs of molecular weight (Mn) above 100,000 g/mol. Preferably the elastomeric mid-block of at least one SBC comprises reactive functionalities, such as double bonds, for example, carbon-carbon double bonds, to enable chemical crosslinking.

The polymer miscible with the polystyrene end blocks may be a polymer capable of forming, to a certain extent, an intimate blend at the molecular level with the polystyrene end blocks. The miscible polymer may be a polymer that is miscible with polystyrene, that is, the SBC and the miscible polymer can form a homogeneous blend, either by chemical similarity and/or by specific interactions, such as between π bonds in arene rings. The interactions may be non-covalent in nature. The interactions may not include covalent bonds between the SBC and the miscible polymer.

Preferably, the number average molecular weight of the miscible polymer (Mn) is below 10,000 g/mol and more preferably below 3,000 g/mol.

Preferably, the miscible polymer has a broad molecular weight polydispersity index, for example greater than 2.0, or greater than 3.0, or greater than 4.0, or greater than 5.0. The miscible polymer preferably has a polarity similar to that of polystyrene.

In a preferred embodiment, the miscible polymers are selected from low molecular weight copolymers of alkyl arene monomers.

The miscible polymer may be selected from the group consisting of polystyrene resin, coumarone-indene resin, polyindene resin, poly(methylindene) resin, vinyltoluene-alphamethylstyrene resin, alphamethylstyrene resin, polyphenylene ether, copolymers of alkyl arene monomers such as alpha methyl styrene and para methyl styrene, rosin ester, styrenated terpenes, polyterpenes, terpene phenolics and mixtures thereof.

The crosslinking agent may be selected from the group consisting of aromatic, aliphatic and heteroatomic monomers and oligomers containing at least two carbon-carbon double bonds, such as, for example: multifunctional acrylates, such as trimethylolpropane triacrylate (TMPTA), trimethylolpropane trimethacrylate (TMPTMA), epoxy acrylates, urethane acrylates, triallyl-cyanurate, triallyl-isocyanurate, functional thiols, such as 1,8-dimercapto-3,6-dioxaoctane, trimethylolpropane-tris-3 mercaptopropionate, pentaerythritol tetrakis-3-mercaptopropionate, ethoxylated trimethylolpropane tri(3-mercaptopropionate), as well as other multifunctional compounds with vinyl or allyl groups, and mixtures thereof.

The crosslinking agent may also be a metal salt, an amine cross-linker selected from the group consisting of organic amine, organic diamine and organic polyamine or a polyol.

The chemical crosslinking may also be performed through so-called "vulcanization", and in this case the crosslinking agent may be selected from conventional sulphur, metallic oxides and accelerators commonly utilized for vulcanization of rubber in thin walled elastic films such as condoms and gloves. Vulcanization is not considered as a preferred crosslinking route in respect of the present disclosure because the accelerators, which are strong skin sensitizers, are not integrated into the chemical network and may bloom to the surface.

In a preferred embodiment, the cross-linking reaction is a thiol-ene reaction. A thiol-ene reaction is a so-called "click" reaction that can take place as a radical-mediated addition reaction.

Preferably the cross-linker is selected from, for example, di-thiol, tri-thiol and tetra-thiol molecules containing ether or ester groups in their backbone.

Advantageously, the cross-linking reaction may be triggered by radiation, for example UV, gamma irradiation, X-Ray or electron beam radiation. Radiation offers multiple advantages: the energy is high enough to create radicals from the existing chemicals, there is less risk of shadowing effects as may be observed with UV curing, and the technology also offers good and accurate control of the dose. It should also be noted that most surgical gloves are sterilized by radiation (either electron beam or gamma radiation) therefore the crosslinking may advantageously occur during the same process as the glove sterilization itself.

In another embodiment, the cross-linking reaction may be initiated or enhanced by one or a mixture of radical-type photo-initiators.

When used, the photo-initiator is preferably selected from those compounds offering broad UV absorption spectra and effective production of reactive radicals upon irradiation, combined with good solubility in resin systems, as well as good tolerance when in contact with human skin. The photo-initiator may, for example, be selected from the group consisting of acylphosphine oxides, for example monoacylphosphine oxides, bisacylphosphine oxides, 2,4,6-trimethylbezoyldiphenylphosphine oxide or others such as 2-hydroxy-methyl-1-phenylpropanone, methylbenzoylformate, and phenylglyoxylic acid methyl ester.

The plasticizer may enhance the stretching and flexibility of the herein disclosed SBC compositions and polymer blends. Preferably, the plasticizer consists of a liquid or a mixture of liquid saturated polyolefins compatible with the midblock (elastomeric block) of the SBC. More preferably the said plasticizer may be selected from compounds that have a pour point less than or equal to 35° C. In the context of the present disclosure it is preferable to use plasticizing oils, preferably mineral plasticizing oils and especially mineral oils formed from a purified mixture of liquid saturated hydrocarbons formed from compounds of paraffinic or naphthenic nature or mixtures thereof in varying proportions.

Preferred plasticizing mineral oils are crystal clear, water-white products that contain no toxic impurities and no MOAH (Mineral Oil Aromatic Hydrocarbon) and comply with USA FDA 21 CFR 178.3620(a), White Mineral Oil, US Pharmacopeia, European Pharmacopoeia (Liquid Paraffin) as well as Europe Regulation (EU) 10/2011 on plastic material and articles intended to come into contact with foodstuff, White mineral oil. A preferred mineral oil is a medicinal white oil which has a specific gravity of 0.85-0.90 at 15° C.

The plasticizer may also be an oligomer or other elastomer that possess a sufficient compatibility with the rubbery mid-blocks and in this case, may be considered more as a "flexibilizer". Such a flexibilizer may be selected from the family of polybutadiene, polyisoprene, polyisobutene, amorphous polyolefin copolymers of propylene and ethylene, butyl rubber and other polymers known to have a sufficient compatibility with the rubbery block. Functionalized or reactive flexibilizers such as acrylic or hydroxyl modified polybutadiene may also be used. These reactive flexibilizers may participate in the chemically crosslinked network.

SBC compositions or miscible polymer blends in accordance with embodiments of the present disclosure are expressed in PHR (Per Hundred Rubber) with rubber being the one or more SBCs. Exemplary ranges for components in the compositions include:

Miscible polymer: 0.25 to 100 phr, preferably 5 to 50 phr
    Plasticizer/Flexibilizer: 0 to 200 phr, preferably 20 to 75 phr
    Cross-linking agent: 0.01 to 5 phr, preferably 0.05 to 1 phr
    Photo-initiator: 0 to 5 phr, preferably 0 to 2 phr.

In another aspect, there is provided a method for producing an immersion article from at least one SBC composition or miscible polymer blend as herein disclosed in which a mold with an external contour which corresponds to that of the immersion article to be produced is immersed for a pre-specifiable period of time in an immersion solution comprising the one or more SBC compositions or miscible polymer blends, and where subsequently the immersion article is removed from the solution and dried.

The article, particularly the dried article may subsequently be exposed to radiation, for example electron beam, gamma, UV or X-Ray radiation.

In another aspect, there is provided a thin film comprising one or more SBC compositions or miscible polymer blends wherein said thin film has a tensile strength of greater than 17 MPa measured according to ASTM 3577 and wherein said thin film is substantially insoluble in an organic solvent.

By "substantially insoluble" it may be meant, for example, that at least 80% of the thin film is insoluble, or at least 95% of the film is insoluble in organic solvents that may be used in the medical field such as methyl methacrylate (MMA) or diethyl ether.

In another aspect, there is provided an elastomeric styrenic block copolymer composition or miscible polymer blend wherein said composition has a tensile strength of at least 17 MPa and wherein said composition is substantially insoluble in an organic solvent By "substantially insoluble" it may be meant, for example, that at least 80% of the composition is insoluble, or at least 95% of the composition is insoluble in organic solvents that may be used in medical fields, such as methyl methacrylate (MMA) or diethyl ether.

In another aspect, there is provided a thin film comprising one or more SBC compositions or miscible polymer blends according to any one of the herein disclosed embodiments.

In any of the herein disclosed embodiments the thin film may have a thickness between about 10 microns and about 500 microns or between about 150 microns and about 250 microns.

In any of the herein disclosed embodiments the thin film may have a thickness less than 500 microns, or less than 400 microns or less than 300 microns or less than 200 microns.

In another aspect, there is provided a multilayer film, said multilayer film comprising one or more layers or thin films, said one or more layers or thin films comprising the herein disclosed SBC compositions or miscible polymer blends.

In another aspect, there is provided a multilayer film, said multilayer film comprising one or more layers or thin films, said one or more layers or thin films comprising SBC compositions or miscible polymer blends, wherein said composition or miscible polymer blend has a tensile strength of at least 17 MPa and wherein said composition or miscible polymer blend is substantially insoluble in an organic solvent.

The multilayer film may be obtained by superposition of several thin layers made from the same SBC composition, or different SBC compositions. Different SBC compositions as presently disclosed may be combined in different layers. Also, at least one layer having the presently disclosed compositions may be combined with other elastomer(s) selected from the group consisting of natural rubber, polybutadiene, polyisoprene, polychloroprene, butyl rubber, polyurethane, acrylic polymers and copolymers, silicone elastomers, other SBCs, cyclic block copolymers (CBC) and blends therefrom. It is understood that the nature of the elastomer(s) constituting each of the said layers may be identical to or different from each other.

According to the present disclosure, SBS, SEBS and butyl rubber are preferred constituents of a multilayer film. In one embodiment, a multilayer glove comprising superposed layers made from the herein disclosed compositions and butyl rubber offers increased resistance to permeation of chemicals such as methyl methacrylate monomer. Such gloves may comprise, for example, a thin butyl rubber layer on the outside layer or/and sandwiched in the middle of other layers comprising the presently disclosed composition of SBC.

Each of the layers comprising the thin-walled elastic film may also comprise other adjuvants conventionally used in the polymer industry and specifically in the glove industry, such as, for example, lubricants and anti-tack agents, antistatic agents, primary and secondary antioxidants, colorants, processing agents and so forth.

In another aspect, there is provided an article of manufacture comprising one or more of the SBC compositions or miscible polymer blends as disclosed herein.

The article of manufacture may be a medical device, such as medical glove, a condom or personal protective equipment, such as laboratory gloves or clean industry gloves.

The film or multilayer film may also include active chemical substances.

The nature of this active substance may be chosen as a function of the properties that are desired. This active chemical substance may be chosen especially from anticorrosion agents, lubricants, chemical markers, phase-change products, energetic-particle (radiation) decelerators, agents with disinfecting power, odoriferous agents or moisturizers, dyes for detecting cuts, metallic particles, and mixtures thereof.

When the active chemical substance is a product with disinfecting power, it is preferably chosen from substances capable of causing a virtually instantaneous denaturation of proteins by simple contact, either by chemical reaction or by a physicochemical effect such as a modification of the surface tension. Among such substances, mention may be made especially of biocides, such as quaternary ammoniums and more particularly dimethyldidecylammonium chloride and benzalkonium chloride, biguanides such as water-soluble salts of chlorhexidine, for instance chlorhexidine digluconate, phthalaldehyde, phenolic derivatives such as hexachlorophene or benzylic derivatives, formaldehyde, nonionic surfactants comprising at least one polyoxyethylene sequence such as octoxynol (Triton®X100), hexamidine, iodinated polyvinylpyrrolidone compounds, nonionic surfactants with virucidal activity, sodium and potassium dichromates and hypochlorites, and mixtures thereof.

The present disclosure is related to compositions comprising SBCs capable of forming chemically and physically crosslinked thin-walled elastic articles with improved mechanical properties.

DETAILED DESCRIPTION OF THE INVENTION

Before the present compositions, components, articles and/or methods are disclosed and described, it is to be understood that unless otherwise indicated this invention is not limited to specific compositions, components, articles, methods, or the like, as such may vary, unless otherwise specified. It is also to be understood that the terminology used herein is for the purpose of describing particular embodiments only and is not intended to be limiting.

It must also be noted that, as used in the specification and the appended claims, the singular forms 'a', 'an' and 'the' include plural referents unless otherwise specified. Thus, for example, reference to a 'SBC' may include more than one SBC, and the like.

Disclosed herein are advantageous SBC compositions and miscible polymer blends and methods for their preparation.

In an exemplary embodiment, there is provided an elastomeric styrenic block copolymer (SBC) composition comprising one or more SBCs and one or more polymers miscible with styrenic end blocks of the one or more SBCs; wherein said block copolymer composition is both physically and chemically crosslinked;
wherein said chemical crosslinking comprises covalent bonds between chains of SBC;
wherein said physical crosslinking comprises non-covalent interaction between styrenic end blocks of the one or more SBCs and the one or more polymers miscible with the styrenic end blocks;
wherein the one or more SBCs is selected from the group consisting of SIS, SBS, SIBS, S-isobutylene-S, SEBS, SEPS, SEEPS or a SBC functionalized with reactive groups grafted in the middle rubber block such as, for example, carboxylic acid, amine, alcohol, maleic anhydride, epoxy, isocyanate and aziridine groups or mixtures thereof; and
wherein the one or more miscible polymers is selected from the group consisting of polystyrene resin, coumarone-indene resin, polyindene resin, poly(methylindene) resin, vinyltoluene-alphamethylstyrene resin, alphamethylstyrene resin, polyphenylene ether, copolymers of alkyl arene monomers such as alpha methyl styrene and para methyl styrene, rosin ester, styrenated terpenes, polyterpenes, terpene phenolics and mixtures thereof.

In another exemplary embodiment there is provided an elastomeric styrenic block copolymer (SBC) composition comprising one or more SBCs and one or more polymers miscible with styrenic end blocks of the one or more SBCs; wherein said block copolymer composition is both physically and chemically crosslinked;
wherein said chemical crosslinking comprises covalent bonds between chains of SBC;
wherein said physical crosslinking comprises non-covalent interaction between styrenic end blocks of the one or more SBCs and the one or more polymers miscible with the styrenic end blocks;
wherein the one or more SBCs is selected from the group consisting of SIS, SBS, SIBS, S-isobutylene-S, SEBS, SEPS, SEEPS or a SBC functionalized with reactive groups grafted in the middle rubber block such as, for example, carboxylic acid, amine, alcohol, maleic anhydride, epoxy, isocyanate and aziridine groups or mixtures thereof; and
wherein the one or more miscible polymers is selected from the group consisting of polystyrene resin, coumarone-indene resin, polyindene resin, poly(methylindene) resin, vinyltoluene-alphamethylstyrene resin, alphamethylstyrene resin, polyphenylene ether, copolymers of alkyl arene monomers such as alpha methyl styrene and para methyl styrene, rosin ester, styrenated terpenes, polyterpenes, terpene phenolics and mixtures thereof, said SBCs having a molecular weight (Mn) above 100,000 g/mol and said miscible polymers having a molecular weight (Mn) less than 10,000 g/mol.

In another exemplary embodiment there is provided an elastomeric styrenic block copolymer (SBC) composition comprising one or more SBCs and one or more polymers miscible with styrenic end blocks of the one or more SBCs; wherein said block copolymer composition is both physically and chemically crosslinked;
wherein said chemical crosslinking comprises covalent bonds between chains of SBC;
wherein said physical crosslinking comprises non-covalent interaction between styrenic end blocks of the one or more SBCs and the one or more polymers miscible with the styrenic end blocks;
wherein at least one SBC comprises, in its elastomeric mid-block, reactive functionalities, such as double bonds, to enable chemical crosslinking; and
wherein the one or more miscible polymers is selected from the group consisting of polystyrene resin, coumarone-indene resin, polyindene resin, poly(methylindene) resin, vinyltoluene-alphamethylstyrene resin, alphamethylstyrene resin, polyphenylene ether, copolymers of alkyl arene monomers such as alpha methyl styrene and para methyl styrene, rosin ester, styrenated terpenes, polyterpenes, terpene phenolics and mixtures thereof, said SBCs having a molecular weight (Mn) above 100,000 g/mol and said miscible polymers having a molecular weight (Mn) less than 10,000 g/mol.

In another exemplary embodiment there is provided an elastomeric styrenic block copolymer (SBC) composition comprising one or more SBCs and one or more polymers miscible with styrenic end blocks of the one or more SBCs; wherein said block copolymer composition is both physically and chemically crosslinked;
wherein said chemical crosslinking comprises covalent bonds between chains of SBC;
wherein said physical crosslinking comprises non-covalent interaction between styrenic end blocks of the one or more SBCs and the one or more polymers miscible with the styrenic end blocks;
wherein at least one SBC comprises, in its elastomeric mid-block, reactive functionalities, such as double bonds, to enable chemical crosslinking; and
wherein the one or more miscible polymers is selected from the group consisting of polystyrene resin, alphamethylstyrene resin, copolymers of alkyl arene monomers such as alpha methyl styrene and para methyl styrene and mixtures thereof, said SBCs having a molecular weight (Mn) above 100,000 g/mol and said miscible polymers having a molecular weight (Mn) less than 10,000 g/mol.

In another exemplary embodiment, there is provided a miscible polymer blend comprising one or more SBCs and one or more polymers miscible with styrenic end blocks of the one or more SBCs;
wherein said miscible polymer blend is both physically and chemically crosslinked;
wherein said chemical crosslinking comprises covalent bonds between chains of SBC;
wherein said physical crosslinking comprises non-covalent interaction between styrenic end blocks of the one or more SBCs and the one or more polymers miscible with the styrenic end blocks;
wherein the one or more SBCs is selected from the group consisting of SIS, SBS, SIBS, S-isobutylene-S, SEBS, SEPS, SEEPS or a SBC functionalized with reactive groups grafted in the middle rubber block such as, for example, carboxylic acid, amine, alcohol, maleic anhydride, epoxy, isocyanate and aziridine groups or mixtures thereof; and
wherein the one or more miscible polymers is selected from the group consisting of polystyrene resin, coumarone-indene resin, polyindene resin, poly(methylindene) resin, vinyltoluene-alphamethylstyrene resin, alphamethylstyrene resin, polyphenylene ether, copolymers of alkyl arene monomers such as alpha methyl styrene and para methyl styrene, rosin ester, styrenated terpenes, polyterpenes, terpene phenolics and mixtures thereof.

In another exemplary embodiment there is provided a miscible polymer blend comprising one or more SBCs and one or more polymers miscible with styrenic end blocks of the one or more SBCs;
wherein said miscible polymer blend is both physically and chemically crosslinked;
wherein said chemical crosslinking comprises covalent bonds between chains of SBC;
wherein said physical crosslinking comprises non-covalent interaction between styrenic end blocks of the one or more SBCs and the one or more polymers miscible with the styrenic end blocks;
wherein the one or more SBCs is selected from the group consisting of SIS, SBS, SIBS, S-isobutylene-S, SEBS, SEPS, SEEPS or a SBC functionalized with reactive groups grafted in the middle rubber block such as, for example, carboxylic acid, amine, alcohol, maleic anhydride, epoxy, isocyanate and aziridine groups or mixtures thereof; and
wherein the one or more miscible polymers is selected from the group consisting of polystyrene resin, coumarone-indene resin, polyindene resin, poly(methylindene) resin, vinyltoluene-alphamethylstyrene resin, alphamethylstyrene resin, polyphenylene ether, copolymers of alkyl arene monomers such as alpha methyl styrene and para methyl styrene, rosin ester, styrenated terpenes, polyterpenes, terpene phenolics and mixtures thereof, said SBCs having a molecular weight (Mn) above 100,000 g/mol and said miscible polymers having a molecular weight (Mn) less than 10,000 g/mol.

In another exemplary embodiment, there is provided a miscible polymer blend comprising one or more SBCs and one or more polymers miscible with styrenic end blocks of the one or more SBCs;
wherein said miscible polymer blend is both physically and chemically crosslinked;
wherein said chemical crosslinking comprises covalent bonds between chains of SBC;
wherein said physical crosslinking comprises non-covalent interaction between styrenic end blocks of the one or more SBCs and the one or more polymers miscible with the styrenic end blocks;
wherein at least one SBC comprises, in its elastomeric mid-block, reactive functionalities, such as double bonds, to enable chemical crosslinking; and
wherein the one or more miscible polymers is selected from the group consisting of polystyrene resin, coumarone-indene resin, polyindene resin, poly(methylindene) resin, vinyltoluene-alphamethylstyrene resin, alphamethylstyrene resin, polyphenylene ether, copolymers of alkyl arene monomers such as alpha methyl styrene and para methyl styrene, rosin ester, styrenated terpenes, polyterpenes, terpene phenolics and mixtures thereof, said SBCs having a molecular weight (Mn) above 100,000 g/mol and said miscible polymers having a molecular weight (Mn) less than 10,000 g/mol.

In another exemplary embodiment there is provided a miscible polymer blend comprising one or more SBCs and one or more polymers miscible with styrenic end blocks of the one or more SBCs;
wherein said miscible polymer blend is both physically and chemically crosslinked;
wherein said chemical crosslinking comprises covalent bonds between chains of SBC;
wherein said physical crosslinking comprises non-covalent interaction between styrenic end blocks of the one or more SBCs and the one or more polymers miscible with the styrenic end blocks;
wherein at least one SBC comprises, in its elastomeric mid-block, reactive functionalities, such as double bonds, to enable chemical crosslinking; and
wherein the one or more miscible polymers is selected from the group consisting of polystyrene resin, alphamethylstyrene resin, copolymers of alkyl arene monomers such as alpha methyl styrene and para methyl styrene, and mixtures thereof, said SBCs having a molecular weight (Mn) above 100,000 g/mol and said miscible polymers having a molecular weight (Mn) less than 10,000 g/mol.

In another exemplary embodiment, there is provided an elastomeric styrenic block copolymer composition comprising:
(a) one or more SBCs;
(b) one or more polymers miscible with polystyrene end blocks of the one or more SBCs; and
(c) one or more cross-linking agents capable of inducing covalent bonding between chains of the one or more SBCs;
wherein the one or more SBCs is selected from the group consisting of SIS, SBS, SIBS, S-isobutylene-S, SEBS, SEPS, SEEPS or a SBC functionalized with reactive groups grafted in the middle rubber block such as, for example, carboxylic acid, amine, alcohol, maleic anhydride, epoxy, isocyanate and aziridine groups or mixtures thereof;
wherein the one or more miscible polymers is selected from the group consisting of polystyrene resin, coumarone-indene resin, polyindene resin, poly(methylindene) resin, vinyltoluene-alphamethylstyrene resin, alphamethylstyrene resin, polyphenylene ether, copolymers of alkyl arene monomers such as alpha methyl styrene and para methyl styrene, rosin ester, styrenated terpenes, polyterpenes, terpene phenolics and mixtures thereof; and
wherein the one or more cross-linking agents is selected from the group consisting of aromatic, aliphatic and heteroatomic monomers and oligomers containing at least two carbon-carbon double bonds, such as, for example: multifunctional acrylates, such as trimethylolpropane triacrylate (TMPTA), trimethylolpropane trimethacrylate (TMPTMA), epoxy acrylates, urethane acrylates, triallyl-cyanurate, triallyl-isocyanurate, functional thiols, such as 1,8-dimercapto-3,6-dioxaoctane, trimethylolpropane-tris-3 mercaptopropionate, pentaerythritol tetrakis-3-mercaptopropionate, ethoxylated trimethylolpropane tri(3-mercaptopropionate), as well as other multifunctional compounds with vinyl or allyl groups, and mixtures thereof.

In another exemplary embodiment, there is provided an elastomeric styrenic block copolymer composition comprising:
(a) one or more SBCs;
(b) one or more polymers miscible with polystyrene end blocks of the one or more SBCs; and
(c) one or more cross-linking agents capable of inducing covalent bonding between chains of the one or more SBCs;
wherein the one or more SBCs is selected from the group consisting of SIS, SBS, SIBS, S-isobutylene-S, SEBS, SEPS, SEEPS or a SBC functionalized with reactive groups grafted in the middle rubber block such as, for example, carboxylic acid, amine, alcohol, maleic anhydride, epoxy, isocyanate and aziridine groups or mixtures thereof;
wherein the one or more miscible polymers is selected from the group consisting of polystyrene resin, coumarone-indene resin, polyindene resin, poly(methylindene) resin, vinyltoluene-alphamethylstyrene resin, alphamethylstyrene resin, polyphenylene ether, copolymers of alkyl arene monomers such as alpha methyl styrene and para methyl styrene, rosin ester, styrenated terpenes, polyterpenes, terpene phenolics and mixtures thereof; and wherein the one or more cross-linking agents is selected from the group consisting of aromatic, aliphatic and heteroatomic monomers and oligomers containing at least two carbon-carbon double bonds, such as, for example: multifunctional acrylates, such as trimethylolpropane triacrylate (TMPTA), trimethylolpropane trimethacrylate (TMPTMA), epoxy acrylates, urethane acrylates, triallyl-cyanurate, triallyl-isocyanurate, functional thiols, such as 1,8-dimercapto-3,6-dioxaoctane, trimethylolpropane-tris-3 mercaptopropionate, pentaerythritol tetrakis-3-mercaptopropionate, ethoxylated trimethylolpropane tri(3-mercaptopropionate), as well as other multifunctional compounds with vinyl or allyl groups, and mixtures thereof, said SBCs having a molecular weight (Mn) above 100,000 g/mol and said miscible polymers having a molecular weight (Mn) less than 10,000 g/mol.

In another exemplary embodiment, there is provided an elastomeric styrenic block copolymer composition comprising:
(a) one or more SBCs;
(b) one or more polymers miscible with polystyrene end blocks of the one or more SBCs; and
(c) one or more cross-linking agents capable of inducing covalent bonding between chains of the one or more SBCs;

wherein at least one SBC comprises, in its elastomeric mid-block, reactive functionalities, such as double bonds, to enable chemical crosslinking; and wherein the one or more miscible polymers is selected from the group consisting of polystyrene resin, coumarone-indene resin, polyindene resin, poly(methylindene) resin, vinyltoluene-alphamethylstyrene resin, alphamethylstyrene resin, polyphenylene ether, copolymers of alkyl arene monomers such as alpha methyl styrene and para methyl styrene, rosin ester, styrenated terpenes, polyterpenes, terpene phenolics and mixtures thereof; and wherein the one or more cross-linking agents is selected from the group consisting of aromatic, aliphatic and heteroatomic monomers and oligomers containing at least two carbon-carbon double bonds, such as, for example: multifunctional acrylates, such as trimethylolpropane triacrylate (TMPTA), trimethyloipropane trimethacrylate (TMPTMA), epoxy acrylates, urethane acrylates, triallyl-cyanurate, triallyl-isocyanurate, functional thiols, such as 1,8-dimercapto-3,6-dioxaoctane, trimethylolpropane-tris-3 mercaptopropionate, pentaerythritol tetrakis-3-mercaptopropionate, ethoxylated trimethylolpropane tri(3-mercaptopropionate), as well as other multifunctional compounds with vinyl or allyl groups, and mixtures thereof, said SBCs having a molecular weight (Mn) above 100,000 g/mol and said miscible polymers having a molecular weight (Mn) less than 10,000 g/mol.

In another exemplary embodiment there is provided an elastomeric styrenic block copolymer composition comprising:
(a) one or more SBCs;
(b) one or more polymers miscible with polystyrene end blocks of the one or more SBCs; and
(c) one or more cross-linking agents capable of inducing covalent bonding between chains of the one or more SBCs;

wherein at least one SBC comprises, in its elastomeric mid-block, reactive functionalities, such as double bonds, to enable chemical crosslinking; and wherein the one or more miscible polymers is selected from the group consisting of polystyrene resin, alphamethylstyrene resin, copolymers of alkyl arene monomers such as alpha methyl styrene and para methyl styrene and mixtures thereof; and wherein the one or more cross-linking agents is selected from the group consisting of aromatic, aliphatic and heteroatomic monomers and oligomers containing at least two carbon-carbon double bonds, such as, for example: multifunctional acrylates, such as trimethylolpropane triacrylate (TMPTA), trimethylolpropane trimethacrylate (TMPTMA), epoxy acrylates, urethane acrylates, triallyl-cyanurate, triallyl-isocyanurate, functional thiols, such as 1,8-dimercapto-3,6-dioxaoctane, trimethylolpropane-tris-3 mercaptopropionate, pentaerythritol tetrakis-3-mercaptopropionate, ethoxylated trimethylolpropane tri(3-mercaptopropionate), as well as other multifunctional compounds with vinyl or allyl groups, and mixtures thereof, said SBCs having a molecular weight (Mn) above 100,000 g/mol and said miscible polymers having a molecular weight (Mn) less than 10,000 g/mol.

In another exemplary embodiment, the layers comprising the thin-walled elastic film may also comprise other adjuvants conventionally used in the polymer industry and specifically in the glove industry, such as, for example, lubricants, anti-tack agents, anti-static agents, primary and secondary antioxidants, colorants, processing agents and so forth.

In another exemplary embodiment, there is provided an elastomeric styrenic block copolymer composition comprising:
(a) one or more SBCs;
(b) one or more polymers miscible with polystyrene end blocks of the one or more SBCs; and
(c) one or more cross-linking agents capable of inducing covalent bonding between chains of the one or more SBCs;

wherein the one or more SBCs is selected from the group consisting of SIS or SBS or mixtures thereof;

wherein at least one SBC comprises, in its elastomeric mid-block, reactive functionalities, such as double bonds, to enable chemical crosslinking; and wherein the one or more miscible polymers is selected from the group consisting of polystyrene resin, alphamethylstyrene resin, copolymers of alkyl arene monomers such as alpha methyl styrene and para methyl styrene and mixtures thereof; and wherein the one or more cross-linking agents is selected from the group consisting of functional thiols, such as 1,8-dimercapto-3,6-dioxaoctane, trimethylolpropane-tris-3 mercaptopropionate, pentaerythritol tetrakis-3-mercaptopropionate, ethoxylated trimethylolpropane tri(3-mercaptopropionate), and mixtures thereof, said SBCs having a molecular weight (Mn) above 100,000 g/mol and said miscible polymers having a molecular weight (Mn) less than 10,000 g/mol.

In another exemplary embodiment, there is provided a method of preparing a SBC composition comprising the step of: combining one or more SBCs, one or more polymers miscible with one or more polystyrene end blocks of the one or more SBCs; and one or more cross-linking agents capable of inducing covalent bonding between chains of the one or more SBCs;

wherein the one or more SBCs is selected from the group consisting of SIS, SBS, SIBS, S-isobutylene-S, SEBS, SEPS, SEEPS or a SBC functionalized with reactive groups grafted in the middle rubber block such as, for example, carboxylic acid, amine, alcohol, maleic anhydride, epoxy, isocyanate and aziridine groups or mixtures thereof;

wherein the one or more miscible polymers is selected from the group consisting of polystyrene resin, coumarone-indene resin, polyindene resin, poly(methylindene) resin, vinyltoluene-alphamethylstyrene resin, alphamethylstyrene resin, polyphenylene ether, copolymers of alkyl arene monomers such as alpha methyl styrene and para methyl styrene, rosin ester, styrenated terpenes, polyterpenes, terpene phenolics and mixtures thereof; and wherein the one or more cross-linking agents is selected from the group consisting of aromatic, aliphatic and heteroatomic monomers and oligomers containing at least two carbon-carbon double bonds, such as, for example: multifunctional acrylates, such as trimethylolpropane triacrylate (TMPTA), trimethylolpropane trimethacrylate (TMPTMA), epoxy acrylates, urethane acrylates, triallyl-cyanurate, triallyl-isocyanurate, functional thiols, such as 1,8-dimercapto-3,6-dioxaoctane, trimethylolpropane-tris-3 mercaptopropionate, pentaerythritol tetrakis-3-mercaptopropionate, ethoxylated trimethylolpropane tri(3-mercaptopropionate), as well as other multifunctional compounds with vinyl or allyl groups, and mixtures thereof.

In another exemplary embodiment, there is provided a method of preparing a SBC composition comprising the step of: combining one or more SBCs, one or more polymers miscible with one or more polystyrene end blocks of the one or more SBCs; and one or more cross-linking agents capable of inducing covalent bonding between chains of the one or more SBCs;

wherein the one or more SBCs is selected from the group consisting of SIS, SBS, SIBS, S-isobutylene-S, SEBS, SEPS, SEEPS or a SBC functionalized with reactive groups grafted in the middle rubber block such as, for example, carboxylic acid, amine, alcohol, maleic anhydride, epoxy, isocyanate and aziridine groups or mixtures thereof;

wherein the one or more miscible polymers is selected from the group consisting of polystyrene resin, coumarone-indene resin, polyindene resin, poly(methylindene) resin, vinyltoluene-alphamethylstyrene resin, alphamethylstyrene resin, polyphenylene ether, copolymers of alkyl arene monomers such as alpha methyl styrene and para methyl styrene, rosin ester, styrenated terpenes, polyterpenes, terpene phenolics and mixtures thereof; and wherein the one or more cross-linking agents is selected from the group consisting of aromatic, aliphatic and heteroatomic monomers and oligomers containing at least two carbon-carbon double bonds, such as, for example: multifunctional acrylates, such as trimethylolpropane triacrylate (TMPTA), trimethylolpropane trimethacrylate (TMPTMA), epoxy acrylates, urethane acrylates, triallyl-cyanurate, triallyl-isocyanurate, functional thiols, such as 1,8-dimercapto-3,6-dioxaoctane, trimethylolpropane-tris-3 mercaptopropionate, pentaerythritol tetrakis-3-mercaptopropionate, ethoxylated trimethylolpropane tri(3-mercaptopropionate), as well as other multifunctional compounds with vinyl or allyl groups, and mixtures thereof, said SBCs having a molecular weight (Mn) above 100,000 g/mol and said miscible polymers having a molecular weight (Mn) less than 10,000 g/mol.

In another exemplary embodiment, there is provided a method of preparing a SBC composition comprising the step of: combining one or more SBCs, one or more polymers miscible with one or more polystyrene end blocks of the one or more SBCs; and one or more cross-linking agents capable of inducing covalent bonding between chains of the one or more SBCs;

wherein at least one SBC comprises, in its elastomeric mid-block, reactive functionalities, such as double bonds, to enable chemical crosslinking; and wherein the one or more miscible polymers is selected from the group consisting of polystyrene resin, coumarone-indene resin, polyindene resin, poly(methylindene) resin, vinyltoluene-alphamethylstyrene resin, alphamethylstyrene resin, polyphenylene ether, copolymers of alkyl arene monomers such as alpha methyl styrene and para methyl styrene, rosin ester, styrenated terpenes, polyterpenes, terpene phenolics and mixtures thereof; and wherein the one or more cross-linking agents is selected from the group consisting of aromatic, aliphatic and heteroatomic monomers and oligomers containing at least two carbon-carbon double bonds, such as, for example: multifunctional acrylates, such as trimethylolpropane triacrylate (TMPTA), trimethylolpropane trimethacrylate (TMPTMA), epoxy acrylates, urethane acrylates, triallyl-cyanurate, triallyl-isocyanurate, functional thiols, such as 1,8-dimercapto-3,6-dioxaoctane, trimethylolpropane-tris-3 mercaptopropionate, pentaerythritol tetrakis-3-mercaptopropionate, ethoxylated trimethylolpropane tri(3-mercaptopropionate), as well as other multifunctional compounds with vinyl or allyl groups, and mixtures thereof, said SBCs having a molecular weight (Mn) above 100,000 g/mol and said miscible polymers having a molecular weight (Mn) less than 10,000 g/mol.

In another exemplary embodiment, there is provided a method of preparing a SBC composition comprising the step of: combining one or more SBCs, one or more polymers miscible with one or more polystyrene end blocks of the one or more SBCs; and one or more cross-linking agents capable of inducing covalent bonding between chains of the one or more SBCs;

wherein at least one SBC comprises, in its elastomeric mid-block, reactive functionalities, such as double bonds, to enable chemical crosslinking; and wherein the one or more miscible polymers is selected from the group consisting of polystyrene resin, alphamethylstyrene resin, copolymers of alkyl arene monomers such as alpha methyl styrene and para methyl styrene, and mixtures thereof; and wherein the one or more cross-linking agents is selected from the group consisting of aromatic, aliphatic and heteroatomic monomers and oligomers containing at least two carbon-carbon double bonds, such as, for example: multifunctional acrylates, such as trimethylolpropane triacrylate (TMPTA), trimethylolpropane trimethacrylate (TMPTMA), epoxy acrylates, urethane acrylates, triallyl-cyanurate, triallyl-isocyanurate, functional thiols, such as 1,8-dimercapto-3,6-dioxaoctane, trimethylolpropane-tris-3 mercaptopropionate, pentaerythritol tetrakis-3-mercaptopropionate, ethoxylated trimethylolpropane tri(3-mercaptopropionate), as well as other multifunctional compounds with vinyl or allyl groups, and mixtures thereof, said SBCs having a molecular weight (Mn) above 100,000 g/mol and said miscible polymers having a molecular weight (Mn) less than 10,000 g/mol.

In another exemplary embodiment there is provided a method of preparing a SBC composition comprising the step of: combining one or more SBCs, one or more polymers miscible with one or more polystyrene end blocks of the one or more SBCs; and one or more cross-linking agents capable of inducing covalent bonding between chains of the one or more SBCs;

wherein at least one SBC comprises, in its elastomeric mid-block, reactive functionalities, such as double bonds, to enable chemical crosslinking; and wherein the one or more miscible polymers is selected from the group consisting of polystyrene resin, alphamethylstyrene resin, copolymers of alkyl arene monomers such as alpha methyl styrene and para methyl styrene, and mixtures thereof; and wherein the one or more cross-linking agents is selected from the group consisting of functional thiols, such as 1,8-dimercapto-3,6-dioxaoctane, trimethylolpropane-tris-3 mercaptopropionate, pentaerythritol tetrakis-3-mercaptopropionate, ethoxylated trimethylolpropane tri(3-mercaptopropionate), and mixtures thereof, said SBCs having a molecular weight (Mn) above 100,000 g/mol and said miscible polymers having a molecular weight (Mn) less than 10,000 g/mol.

In another exemplary embodiment, there is provided a method for producing an immersion article from at least one SBC composition or miscible polymer blend as disclosed in any one of the herein described exemplary embodiments in which a mold with an external contour which corresponds to that of the immersion article to be produced is immersed for a pre-specifiable period of time in an immersion solution comprising the one or more SBC compositions or miscible polymer blends, and where subsequently the immersion article is removed from the solution and dried.

The article, particularly the dried article, may subsequently be exposed to radiation, for example electron beam, gamma, UV or X-Ray radiation In another exemplary embodiment, there is provided a, thin film comprising one or more SBC compositions or miscible polymer blends as disclosed in any one of the herein described exemplary embodiments wherein said thin film has a tensile strength of greater than 17 MPa measured according to ASTM 3577 and wherein said thin film is substantially insoluble in an organic solvent.

In another exemplary embodiment there is provided a thin film comprising one or more SBC compositions or miscible polymer blends according to any one of the herein disclosed preferred embodiments.

In any of the herein disclosed exemplary embodiments the thin film may have a thickness between about 10 microns and about 500 microns or between about 150 microns and about 250 microns.

In any of the herein disclosed exemplary embodiments the thin film may have a thickness less than 500 microns, or less than 400 microns or less than 300 microns or less than 200 microns.

In another exemplary embodiment, there is provided an article of manufacture, such as a glove or a condom, said article of manufacture comprising one or more SBC compositions or miscible polymer blends as disclosed in any one of the herein disclosed exemplary embodiments.

Mechanical Properties

The SBC compositions or miscible polymer blends according to the present disclosure may have a modulus at 100% elongation below 1.0 MPa or below 0.70 MPa.

Thin-walled elastic articles according to the present disclosure may have a modulus at 100% elongation below 1.0 MPa or below 0.70 MPa.

Thin-walled elastic articles according to the present disclosure may have a force at break compliant with EN455-2 and ISO10282, that is, above 9N (measured on unaged film).

Thin-walled elastic articles according to the present disclosure may have a tensile strength compliant with ASTMD3577, that is, above 17 MPas (unaged film).

The SBC compositions, or miscible polymer blends or thin-walled elastic articles may have any combination of the above disclosed mechanical properties.

Composition

Compositions in accordance with embodiments of the present disclosure are expressed in PHR (Per Hundred Rubber) with rubber being the one or more SBCs. Exemplary ranges for components in the compositions include:

Miscible polymer: 0.25 to 100 phr, preferably 5 to 50 phr
Plasticizer/Flexibilizer: 0 to 200 phr, preferably 20 to 75 phr
Cross-linking agent: 0.01 to 5 phr, preferably 0.05 to 1 phr
Photo-initiator: 0 to 5 phr, preferably 0 to 2 phr.

Definition and Composition

Thin-walled elastic dipped articles, for example gloves, particularly medical gloves, and condoms as disclosed herein may have a thickness in the range from between about 10 to about 500 microns or from about 150 to about 250 microns.

The dipped articles may comprise a single layer or may be multilayered. The multilayered articles may comprise layers comprising the same polymer composition or different polymer compositions.

EXAMPLES

The following Examples describe the compositions according to the present disclosure and are intended to illustrate the disclosure. The Examples are not to be construed as limiting in any way the scope of the present disclosure.

It is to be understood that while the present disclosure has been described in conjunction with the specific embodiments thereof, the foregoing description is intended to illustrate and not limit the scope of the disclosure. Other aspects, advantages and modifications will be apparent to those skilled in the art to which the disclosure pertains. Therefore, the examples are put forth so as to provide those skilled in the art with a complete disclosure and description of how to make and use the disclosed compositions, and are not intended to limit the scope of the disclosure.

Example 1

The following example demonstrates the improved performance (mechanical properties and chemical resistance) of a composition according to the present disclosure.

Styrene-butadiene-styrene copolymer (SBS) with a viscosity in toluene (10% concentration) of 150 mPas at 25° C., miscible polymer based on styrene and substituted styrenes (Mn=800 g/mol, polydispersity index=2.8), plasticizer as a white mineral oil with a viscosity of 68 mPas at 40° C., and a crosslinking agent as trimethylpropane tris (3-mercaptopropionate) were dissolved in a mixture of methylcyclohexane and toluene (8:2) to form a solution having 18% solid content by weight.

Different amounts of crosslinking agents as well as miscible polymer ("P") were used as indicated in the Table below.

The amount of plasticizer was 50 phr and 1 phr of polyphenolic antioxidant was added to the polymer solution.

The solution was stored at ambient temperature in an appropriate vessel covered to prevent solvent evaporation. Films were obtained following solvent evaporation after dipping a porcelain mold into the solution using a dipping robot with controlled dipping speeds. The film was dried at 70° C. for 1 hour before stripping and then a final drying at 50° C. during 6 hours was performed to remove trace amounts of residual solvent.

The film was then exposed to electron beam radiation at a dose of 25±2 kGy.

The chemical resistance of the irradiated film was assessed by different means. Ideally the testing method should reproduce the conditions of real exposure to the chemical.

In the present example, the SBC composition was intended to be used for a glove so the following tests were employed to assess the chemical resistance of the film:
1) swab test: 0.5 g of pure methyl methacrylate monomer was deposited on a cotton swab which was then applied on a film previously brought under slight tension. The contact time was 10 seconds, under slight pressure. The test was repeated three times and then the film resistance was checked.
2) swelling test: a disc of a diameter of 25 mm was cut from the film and placed in a beaker containing 20 ml of MEK for 5 minutes under slight agitation. After 5 minutes, the disc was removed, its external surfaces were cleaned with a tissue and the disk diameter measured. The swelling rate was measured as 100* (diameter after swelling in mm−25)/25.

The mechanical properties were measured according to ASTM 3577 for surgical gloves. For unaged synthetic type II material, the minimum limit of tensile strength is 17 MPa. Results are presented in the following Table:

| Reference | Amount of cross-linker (phr) | Amount of P (phr) | Tensile strength after exposure at 25kGy | Swab test | % swelling |
|---|---|---|---|---|---|
| 1 | 0 | 0 | 12.1 | Film cracks | Soluble |
| 2 | 0 | 10 | 16.5 | Film cracks | Soluble |
| 3 | 0.4 | 10 | 18.2 | No impact on film | 0% |
| 4 | 0.4 | 0 | 8.8 | No impact on film | 0% |

These results indicate that the SBS films can be efficiently chemically crosslinked with trimethylolpropane tris (3-mercaptopropionate).

The example indicates that a composition combining a SBC, a cross-linker and a miscible polymer exhibits a greater mechanical performance than:
the SBC alone (reference 1)
the SBC combined with the miscible polymer without the cross-linker (reference 2)
the SBS combined with the cross-linker without the miscible polymer (reference 4)

Reference 3 also indicates a significantly improved chemical resistance as compared with references 1 or 2. Finally it can be seen that the reference 3 glove is the only sample that passes the ASTM specifications regarding tensile strength. The resulting film is also very soft (modulus at 100% elongation=0.68 MPa).

Example 2

A Styrene-Isoprene-Styrene copolymer (SIS) containing Styrene-Isoprene diblock copolymer, with a viscosity in toluene (10% concentration) of 45 mPa·s at 25° C. was used to replace the SBS copolymer used in the references 1 to 4.

The miscible polymer is based on styrene and substituted styrenes (Mn=800 g/mol, polydispersity index=2.8) at a quantity of 20 phr, and there is no plasticizer nor flexibilizer. The crosslinking agent is trimethylolpropane trimethacrylate used at a quantity of 1 phr.

As for the references 1 to 4, the films were obtained following solvent evaporation then dried to remove any traces of residual solvent before exposure to electron beam radiation at a dose of 50±3 kGy.

The mechanical properties of the film is 17.1 MPa, with excellent chemical resistance on swab test.

Example 3

A multilayer film was produced using the following combinations of polymers:
a first layer with a thickness of 80±10 μm composed of Styrene-Butadiene-Styrene block copolymer composition described in the reference 3 above
a second layer with a thickness of 140±20 μm composed of a high molecular weight Styrene-Ethylene/Butylene-Styrene (SEBS). This SEBS has a radial structure with a viscosity of 75 cp in toluene at 5% and contains 31% of Polystyrene. The miscible polymer is based on styrene and substituted styrenes (Mn=800 g/mol, polydispersity index=2.8) at a quantity of 25 phr and the amount of plasticizer is 60 phr. The crosslinking agent is trimethylpropane tris (3-mercaptopropionate) at a quantity of 0.2 phr.

The multilayer film is exposed to electron-beam at 40 kGy±3.

Analysis of this film showed a tensile strength of 20.5 MPa with an excellent resistance on swab test.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited.

All documents cited are herein fully incorporated by reference for all jurisdictions in which such incorporation is permitted and to the extent such disclosure is consistent with the description of the present disclosure.

The invention claimed is:

1. An elastomeric styrenic block copolymer (SBC) composition comprising one or more SBCs and one or more polymers having a molecular weight polydispersity index greater than 2.0 miscible with styrenic end blocks of the one or more SBCs;
    wherein said block copolymer composition is both physically and chemically crosslinked;
    wherein said chemical crosslinking comprises covalent bonds between chains of SBC and;
    wherein said physical crosslinking comprises non-covalent interaction between styrenic end blocks of the one or more SBCs and the one or more polymers miscible with the styrenic end blocks.

2. The composition according to claim 1, further comprising one or more plasticizers and/or flexibilizers compatible with an elastomeric mid-block of the one or more SBCs.

3. The composition according to claim 2, wherein the plasticizer comprises a liquid or a mixture of liquid saturated polyolefins compatible with the midblock (elastomeric block) of the SBC.

4. The composition according to claim 2, wherein the plasticizer comprises plasticizing oils.

5. The composition according to claim 2, wherein the flexibilizer is selected from polybutadiene, polyisoprene, polyisobutene, amorphous polyolefin copolymers of propylene and ethylene, butyl rubber and other elastomers known to have a sufficient compatibility with the elastomeric block.

6. The composition according to claim 1, wherein, independently, the one or more SBCs comprise a fully unsaturated or fully saturated elastomeric mid-block.

7. The composition according to claim 6, wherein the one or more SBCs comprise a fully saturated elastomeric mid-block, said fully saturated elastomeric mid-block being cleavable when exposed to radiation.

8. The composition according to claim 1, wherein the one or more SBCs is selected from the group consisting of SIS, SBS, SIBS, S-isobutylene-S, SEBS, SEPS, SEEPS or a SBC functionalized with reactive groups grafted in the middle rubber block.

9. The composition according to claim 1, wherein the one or more SBCs has a molecular weight (Mn) above 100,000 g/mol.

10. The composition according to claim 1, wherein at least one SBC has an elastomeric mid-block containing reactive functionalities.

11. The composition according to claim 1, wherein the number average molecular weight of the miscible polymer (Mn) is below 10,000 g/mol.

12. The composition according to claim 1, wherein the one or more miscible polymers have a molecular weight polydispersity index greater than 5.0.

13. The composition according to claim 1, wherein the miscible polymer is selected from the group consisting of polystyrene resin, coumarone-indene resin, polyindene resin, poly(methylindene) resin, vinyltoluene-alphamethylstyrene resin, alphamethylstyrene resin, polyphenylene ether, copolymers of alkyl arene monomers.

14. The composition according to claim 1, wherein at least one SBC comprises, in its elastomeric mid-block, double bonds, to enable chemical crosslinking; and wherein the one or more miscible polymers is selected from the group consisting of polystyrene resin, coumarone-indene resin, polyindene resin, poly(methylindene) resin, vinyltoluene-alphamethylstyrene resin, alphamethylstyrene resin, polyphenylene ether, copolymers of alkyl arene monomers, said SBCs having a molecular weight (Mn) above 100,000 g/mol and said miscible polymers having a molecular weight (Mn) less than 10,000 g/mol.

15. The composition according to claim 1, wherein the block copolymer composition is crosslinked using a crosslinking agent is selected from the group consisting of multifunctional acrylates, functional thiols, as well as other multifunctional compounds with vinyl or allyl groups, and mixtures thereof.

16. The composition according to claim 1, wherein the block copolymer composition is crosslinked using a crosslinking agent is a metal salt, an amine cross-linker selected from the group consisting of organic amine, organic diamine and organic polyamine or a polyol.

17. The composition according to claim 1, wherein the block copolymer composition is crosslinked using a crosslinking agent is selected from conventional sulphur, metallic oxides and accelerators commonly utilized for vulcanization of rubber.

18. The composition according to claim 1, wherein the block copolymer composition is crosslinked using a cross-linker is selected from di-thiol, tri-thiol and tetra-thiol molecules containing ether or ester groups in their backbone.

19. The composition according to claim 1, further comprising an adjuvant.

20. An article of manufacture comprising one or more of the elastomeric SBC compositions according to claim 1.

21. The article of manufacture according to claim 20, wherein the article is a medical device, or personal protective equipment.

22. A method of preparing the elastomeric SBC composition according to claim 1 comprising the step of:
combining the one or more SBCs, the one or more polymers having a molecular weight polydispersity index greater than 2.0 miscible with the one or more polystyrene end blocks of the one or more SBCs; and one or more cross-linking agents capable of inducing covalent bonding between chains of the one or more SBCs.

23. The method according to claim 22, wherein the composition is cross-linked by the application of radiation.

24. The method according to claim 22, wherein the crosslinking reaction is initiated or enhanced by one or a mixture of radical-type photo-initiators.

25. The method according to claim 24, wherein the crosslinking photo-initiators are selected from the group consisting of acylphosphine oxides.

26. A method for producing an immersion article from at least one elastomeric SBC composition according to claim 1, in which a mold with an external contour which corresponds to that of the immersion article to be produced is immersed for a pre-specifiable period of time in an immersion solution comprising the one or more elastomeric SBC compositions, and where subsequently the immersion article is removed from the solution and dried.

27. The method according to claim 26 further comprising exposing the dried article to radiation.

28. A thin film comprising one or more elastomeric SBC compositions according to claim 1, wherein said thin film has a tensile strength of greater than 17 MPa when evaluated according to ASTM 3577 and wherein said thin film is substantially insoluble in an organic solvent.

29. The thin film according to claim 28, wherein at least 80% of the thin film is insoluble, or at least 95% of the film is insoluble in an organic solvent.

30. The thin film according to claim 28, wherein the film has a thickness between about 10 microns and about 500 microns.

31. The thin film according to claim 28, wherein the film has a thickness between about 150 microns and about 250 microns.

32. A multilayer film, said multilayer film comprising several thin films according to claim 28.

33. A multilayer film, said multilayer film comprising one or more layers, said one or more layers comprising one or more elastomeric SBC compositions according to claim 1, wherein said one or more elastomeric SBC compositions has a tensile strength of at least 17 MPa.

34. The multilayer film according to claim 33, wherein at least one layer is selected from the group consisting of natural rubber, polybutadiene, polyisoprene, polychloroprene, butyl rubber, polyurethane, acrylic polymers and copolymers, silicone elastomers, other SBCs, cyclic block copolymers (CBC) and blends therefrom.

35. A miscible polymer blend comprising one or more SBCs and one or more polymers having a molecular weight polydispersity index greater than 2.0 miscible with styrenic end blocks of the one or more SBCs;

wherein said miscible polymer blend is both physically and chemically crosslinked;
wherein said chemical crosslinking comprises covalent bonds between chains of SBC and;
wherein said physical crosslinking comprises non-covalent interaction between styrenic end blocks of the one or more SBCs and the one or more polymers miscible with the styrenic end blocks.

\* \* \* \* \*